(12) United States Patent
Vilarinho Dias

(10) Patent No.: US 7,074,264 B2
(45) Date of Patent: Jul. 11, 2006

(54) FOAMING AQUEOUS COMPOSITION, USE THEREOF AND PROCESS FOR TEMPORARY DEMARCATION OF REGULATION DISTANCES IN SPORTS

(75) Inventor: Heine Allemagne Vilarinho Dias, Minas Gerais (BR)

(73) Assignee: Spuni Comércio de Produtos Esportivos E Marketing Ltda., Rio de Janeiro (BR)

( * ) Notice: Subject to any disclaimer, the term of this patent is extended or adjusted under 35 U.S.C. 154(b) by 29 days.

(21) Appl. No.: 10/239,825

(22) PCT Filed: Mar. 30, 2001

(86) PCT No.: PCT/BR01/00031

§ 371 (c)(1),
(2), (4) Date: Jan. 9, 2003

(87) PCT Pub. No.: WO01/72912

PCT Pub. Date: Oct. 4, 2001

(65) Prior Publication Data

US 2004/0221766 A1   Nov. 11, 2004

(30) Foreign Application Priority Data

Mar. 31, 2000  (BR) .............................. PI 0002743
Oct. 20, 2000  (BR) .............................. PI 0004962

(51) Int. Cl.
*C09D 11/00*   (2006.01)

(52) U.S. Cl. .............................. 106/31.01; 106/31.02; 510/406

(58) Field of Classification Search ............. 106/31.01, 106/31.94, 31.32, 31.64
See application file for complete search history.

(56) References Cited

U.S. PATENT DOCUMENTS 5,711,790 A * 1/1998 Coller ..................... 106/31.01
5,735,940 A * 4/1998 Coller ..................... 106/31.01
5,888,478 A   3/1999 Maurin ....................... 424/45

FOREIGN PATENT DOCUMENTS

FR   2586358 A * 8/1985
JP   06305934     11/1994
JP   08319212     12/1996

* cited by examiner

*Primary Examiner*—John R. Hardee
(74) *Attorney, Agent, or Firm*—Finnegan, Henderson, Farabow, Garrett & Dunner, L.L.P.

(57) ABSTRACT

A foaming composition to temporarily mark and delimit regulation distances on courts and fields of sports that is suitable for use in sport matches and competitions and a process for using it in which it is required to momentarily delimit distances by means of a quick application without any injuries to the place where the competition is occurring, ensuring compliment with the rules and conditions of the matches, and avoiding any doubts or discussions related to the placing of the competitors concerning the minimal distances to be respected.

17 Claims, No Drawings

US 7,074,264 B2

FOAMING AQUEOUS COMPOSITION, USE THEREOF AND PROCESS FOR TEMPORARY DEMARCATION OF REGULATION DISTANCES IN SPORTS

FIELD OF THE INVENTION

The object of the present invention is to provide a foaming aqueous composition to temporarily mark and delimit regulation distances on courts and fields of sports, suitable for use in sport competitions in which it is required to momentarily delimit distances, by means of a quick application, without any injuries on the place where the competition is occuring, ensuring the compliment with the rules and conditions of the matches, avoiding any doubts or discussions related to the placing of the competitors concerning the minimal distances to be respected.

BACKGROUND OF THE INVENTION

U.S. Pat. No. 5,711,790 and U.S. Pat. No. 5,735,940 (Coller) disclose water-based marking compositions which can be removed from a substrate surface. Such compositions comprise water, water-soluble salt or mixtures of water-soluble salts, and colorant(s), and are used for producing colored temporary marks on surfaces, especially snow or ice. However, these markings do not spontaneously disappear from the surface. To be removed, they have to be washed off, for example, by rain or disappear with snow or ice as they melt.

U.S. Pat. No. 6,077,898 (Flores) refers to aqueous aerosol paint compositions comprising a film-forming polymer suitable for temporarily marking tunnels and roads. Like the markings produced by the compositions of U.S. Pat. No. 5,711,790 and U.S. Pat. No. 5,735,940, these markings are also temporary, but they do not disappear by themselves and should be removed with water, for example by rain.

U.S. Pat. No. 5,174,571 (Aubusson, et al.) discloses a method and apparatus for forming temporary visible lines on a surface using laser beams. They are primarily intended for forming the demarcation lines of courts and fields of a number of different sports in a multi-purpose area but in which only the demarcation lines for any one particular sport are visible at any one time.

Documents NL 8801010 e NL 8800622 (Nijenhuis) relates to a system of illuminated markers consisting of bundles of fibre optic cables disposed under a playing area linked to a light generating equipment. Such a system is intended for forming the demarcation lines of courts and fields so that the same place can be used for different games.

OBJECTION OF THE INVENTION

In sports, for example in soccer, there are rules that delimit the distance of the barrier formed by the players of an opposing team when taking a free kick. This barrier should be at a regulation distance away from the ball and should not move in order to reduce such a distance. Since the referee of the match, when delimiting the distance, does not have a point of reference, he is almost unable to check the movement/approaching of the players forming the barrier towards the ball and, therefore, unable to apply the required sanctions.

In addition, it should be pointed out that this kind of occurrence is a moot point all around the world and, since there is not a total control thereon, a lot of teams are prejudiced and the match or competition loses its art or talent, transforming into carelessness and luck.

In view of these problems and with the purpose of overcoming them, the applicant have developed a foaming aqueous composition suitable for temporarily marking and delimiting regulation distances on courts and fields of sports, safeguarding that it is not restrictive only to sports, but it can also be used in messages and homages on walls, grasses, woods, cars, pavements, asphalts, as freedom of speech.

SUMMARY OF THE INVENTION

The present invention refers to a foaming aqueous composition for temporary demarcation of regulation distances in sports, comprising as a foam promoter at least one non ionic or amphoteric surfactant and as a foam controller at least one amphoteric surfactant other than that used as a foam promoter, in combination with at least one propellant.

The present invention also refers to the use of this composition for marking and delimiting regulation distances on courts and fields of sports, in particular on soccer fields.

Another object of the present invention consists of a process for temporary demarcation of regulation distances in sports, comprising the step of spraying on a place of a court or field of sports a foaming aqueous composition of the present invention.

DETAILED DESCRIPTION OF THE INVENTION

In accordance with the present invention, the preferred non ionic surfactants to be used as foam promoters are the ethoxylated vegetable oils, in particular ethoxylated castor oil. Due to its characteristic odor, when ethoxylated castor oil is present in the composition, it is preferred to add a fragrance masking or flavoring agent. Preferably, said fragrance masking or flavoring agent is selected from essential oils.

When an amphoteric surfactant is used as foam promoter, it is preferably an alkyl dimethylamine oxide.

The preferred amphoteric surfactants to be used as foam controllers are the betaines, in particular coco amido propyl betaine.

The foam promoter/controller combination is present in the composition of the present invention in a quantitative ratio effective to provide volatile foam, but which remains active and stable during a period of time sufficient to enable visualization until the act to be performed is finished, for instance, to take a free kick in a soccer match. This period of time will depend on the sport and on the act to be performed. Furthermore, a faster or slower foam decomposition will also depend on the atmospheric, climatic and weather conditions of the place in which the sport is being performed. Usually, the foam composition will remain visible for a period of time ranging from 40 seconds to 3 minutes.

In the practice, we may consider for example a free kick occurred in a soccer match. The referee, by counting steps, estimates the distance wherein the barrier should be positioned in relation to the ball position in order to permit the free kick to be taken. By means of a tube containing the composition for marking and delimiting the regulation distances in courts and fields of sports object of the present invention, he presses the ejector nozzle to release the volatile foam on the grass, tracing a line on the correct place for forming the barrier. In the event one player treads on said line marked by the foam and, accordingly, on the foam, it will be adhered to the player's footwear whereby the referee may apply the suitable sanctions for this circumstance. If, instead of treading on this foam, the player crosses the same, the referee will be able to visualize the proximity of the player in relation to the ball, since his point of reference is indicated on the field, also permitting the application of suitable sanctions for this circumstance.

The foaming aqueous composition of the present invention may further contain other conventional components of foams such as foam thickeners and/or foam stabilizers, which can be selected from alkanolamides, strongly ionizable salts, anionic surfactants, or mixtures thereof. Preferably, coconut fatty acid diethanolamide, sodium chloride, sodium lauryl ether sulfate, or mixtures thereof are used as thickeners and/or foam stabilizers.

For controlling the culturing of bacteria destructing organic compounds in the presence of water, bactericidal agents can also be utilized in the foaming aqueous composition of the present invention. Preferred bactericidal agents for this purpose are selected from the group comprising triazines, triazines, benzoisothiazolinone and chloromethyl isothiazolinone compounds, or mixtures thereof. Triazine is particularly preferred.

The propellant preferred to be used in the composition of the present invention is selected from propane, butane, nitrogen, CO2 gases, or mixture thereof. Particular preference is given to the propane gas used in a range from 4 to 6% by weight.

With a purpose to enable a better visualization, the composition of the present invention may further comprises one or more coloring pigments. The quantitative variation of the components in combination with the pigmentation enables the use of the composition of the present invention in extremely hot or cold weathers, in rainy or sunny days, snow, by night or day, according to the climatic action and intensity of the application.

A preferred formulation for the composition of the present invention comprises 10 to 30% by weight of ethoxylated castor oil, 0.1% to 0.5% by weight of coconut amido propyl betaine, 0.05% to 3.00% by weight of triazine and 0.2% to 0.8% by weight of essence, the balance being water, propellant and, optionally, coloring pigment.

In accordance with another embodiment of the present invention, the composition comprises 0.5 to 3% by weight of alkyl dimethylamine oxide, 1 to 3% by weight of coco amido propyl betaine, 10 to 30% by weight of sodium lauryl ether sulfate, 0.01% to 0.20% by weight of sodium chloride, 1 to 5% by weight of coconut fatty acid diethanolamide, 0.05% to 3.00% by weight of triazine and 4 to 6% by weight of propane gas, the balance being water, propellant and, optionally, coloring pigment.

The composition of the present invention may be packed in a tube, preferably made of aluminum, with an ejector nozzle which, when pressed, causes the foam to release, marking the court or field of sports to delimit the distance previously designated by the referee. The shape of the ejector nozzle, either concerning its diameter or the shape of the tube packing the composition, enables a release of a foam with bigger or smaller, larger or thinner thickness. The escape pipe is preferably reduced in order to provide the output of the foaming composition, even in the position upside down. Aluminum tubes in various sizes, commercially available, are easily carried in the pocket, waist or other part of the referee's clothes, also enabling their utilization several times.

The foaming aqueous composition of the present invention is biodegradable, non-toxic, non-inflammable, residue-free, non-skin damaged and does not damage grasses or others floors. The propellant gas does not affect ozone layer since it does not contain chlorofluorocarbon.

Furthermore, the composition of the present invention does not change any rule of the sport in which the same is used. On the contrary, it is the subside that each referee, athlete, supporter or sporting commentator needs in order to be sure that the rule is being applied and is the same for all.

The following illustrative examples are intended to better describe the present invention. However, illustrated data and procedures only refer to embodiments of the present invention and should not be considered as restricting the scope thereof.

EXAMPLES

All percentages indicated in the examples are percentages by weight, based on the total weight of the composition.

Example 1

A foaming aqueous composition was prepared utilizing, as foam promoter, the non ionic surfactant, ethoxilated castor oil and, as a foam controller the amphoteric surfactant coco amido propyl betaine:

| Component | % by weight |
| --- | --- |
| Ethoxilated castor oil | 20 |
| Coco amido propyl betaine | 0.3 |
| Triazine | 0.2 |
| Essence | 0.5 |
| Water and propellant | Balance to 100% |

Example 2

The foaming aqueous composition of the present invention was prepared utilizing as a foam promoter, the amphoteric surfactant alkyl dimethylamine oxide and, as foam controller, the amphoteric surfactant coco amide propyl betaine:

| Component | % by weight |
| --- | --- |
| Alkyl dimethylamine oxide | 0.6 |
| Coco amido propyl betaine | 2.5 |
| Sodium lauryl ether sulfate | 20 |
| Fatty acid diethanolamide | 3 |
| Sodium chloride | 0.1 |
| Triazine | 0.9 |
| Propane | 4.9 |
| Water | Balance to 100% |

Example 3

A green colored foaming aqueous composition of was prepared utilizing, as a foam promoter, the amphoteric surfactant alkyl dimethylamine oxide and, as a foam controller, the amphoteric surfactant coco amido propyl betaine:

| Component | % by weight |
| --- | --- |
| Alkyl dimethylamine oxide | 2.32 |
| Coco amido propyl betaine | 2.5 |
| Sodium lauryl ether sulfate | 20 |
| Fatty acid diethanolamide | 3 |
| Sodium chloride | 0.18 |
| Triazine | 2 |
| Propane | 6 |
| Light green pigment | 5 |
| Water | Balance to 100% |

The foaming aqueous compositions of the present invention which comprise, as a foam promoter, the amphoteric surfactant alkyl dimethylamine, and, as a foam controller, the amphoteric surfactant coco amido propyl betaine, present the following physical and chemical data:

| | |
| --- | --- |
| Density | 0.910 a 1.120 g/cm3; |
| Color (no pigments added) | slightly yellow or even white; |
| Aspect | clear e homogenous; |
| Viscosity | 7" to 20" CF no. 3; |
| pH | 5.5 to 9.5; |
| Foaming power | 100 ml for 200 ml of foam. |

Being described based on embodiment examples, it must be understood that the present invention covers other configurations, being limited only by the scope of the appended claims.

The invention claimed is:

1. A process for the temporary demarcation of regulation distances in sports, comprising the step of spraying at a place on a court or field of sports a foaming composition containing from 10 to 30% by weight of ethoxylated castor oil as a foam promoter and from 0.1 to 0.5% by weight of coco amido propyl betaine as a foam controller, in combination with at least one propellant.

2. The process according to claim 1, wherein the composition further includes a fragrance masking or flavoring agent.

3. The process according to claim 2, wherein the fragrance masking or flavoring agent is an essential oil.

4. The process according to claim 1, wherein the composition further includes thickeners and foam stabilizers.

5. The process according to claim 4, wherein the thickeners and foam stabilizers are alkanolamides, strongly ionizable salts, anionic surfactants or mixtures thereof.

6. The process according to claim 5, wherein the thickeners and foam stabilizers are coconut fatty acid diethanolamide, sodium chloride, sodium lauryl ether sulfate or mixtures thereof.

7. The process according to claim 1, wherein the composition further includes a bactericidal agent.

8. The process according to claim 7, wherein the bactericidal agent is selected from the group consisting of triazine, benzoisothiazolinone and chloromethyl isothiazolinone compounds, or mixtures thereof.

9. The process according to claim 8, wherein the bactericidal agent is triazine.

10. The process according to claim 1, wherein the propellant is propane gas, butane gas, nitrogen gas, $CO_2$ gas or a mixture thereof.

11. The process according to claim 10, wherein the propellant is propane gas.

12. The process according to claim 1, wherein the controller/promoter combination is present within the composition in a quantitative ratio enough to provide a foam, but which remains active and stable during a period of time ranging from 40 seconds to 3 minutes.

13. The process according to claim 1, wherein the composition includes from 0.05 to 3.00% by weight of triazine and from 0.2 to 0.8% by weight of a fragrance masking or flavoring agent, the balance being water and the propellant.

14. The process according to claim 1, wherein the composition includes from 10 to 30% by weight of sodium lauryl ether sulfate, from 0.01 to 0.20% by weight of sodium chloride, from 1 to 5% by weight of coconut fatty acid diethanolamide and from 0.05 to 3.00% by weight of triazine, the balance being water and the propellant.

15. The process according to claim 1, wherein the composition further includes one or more coloring pigments.

16. The process according to claim 1, wherein the field of sports is a soccer field.

17. A process for the temporary demarcation of regulation distances in sports, comprising the step of spraying at a place on a court or field of sports a foaming composition containing 0.5 to 3% by weight of an alkyl dimethylamine oxide as a foam promoter and from 1 to 3% by weight of coco amido propyl betaine as a foam controller, in combination with at least one propellant.

* * * * *